(12) United States Patent
Al-Ali et al.

(10) Patent No.: US 8,781,549 B2
(45) Date of Patent: Jul. 15, 2014

(54) NONINVASIVE OXIMETRY OPTICAL SENSOR INCLUDING DISPOSABLE AND REUSABLE ELEMENTS

(75) Inventors: Ammar Al-Ali, San Juan Capistrano, CA (US); Yassir Abdul-Hafiz, Irvine, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

(21) Appl. No.: 13/585,669

(22) Filed: Aug. 14, 2012

(65) Prior Publication Data
US 2012/0310061 A1  Dec. 6, 2012

Related U.S. Application Data

(63) Continuation of application No. 11/754,972, filed on May 29, 2007, now Pat. No. 8,244,325, which is a continuation of application No. 11/172,587, filed on Jun. 30, 2005, now Pat. No. 7,225,007, which is a continuation of application No. 10/351,645, filed on Jan. 24, 2003, now Pat. No. 6,920,345.

(51) Int. Cl.
*A61B 5/1455* (2006.01)

(52) U.S. Cl.
USPC .......................................... 600/344; 600/323

(58) Field of Classification Search
USPC ........................ 600/310, 322, 323, 340, 344
See application file for complete search history.

(56) References Cited

U.S. PATENT DOCUMENTS

| | | |
|---|---|---|
| 4,621,643 A | 11/1986 | New, Jr. et al. |
| 4,685,464 A | 8/1987 | Goldberger et al. |
| 4,700,708 A | 10/1987 | New, Jr. et al. |
| 4,830,014 A | 5/1989 | Goodman et al. |
| 4,865,038 A | 9/1989 | Rich et al. |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,090,410 A | 2/1992 | Saper et al. |
| 5,094,240 A | 3/1992 | Muz |
| 5,158,323 A | 10/1992 | Yamamoto et al. |
| 5,163,438 A | 11/1992 | Gordon et al. |
| 5,170,786 A | 12/1992 | Thomas et al. |
| 5,209,230 A | 5/1993 | Swedlow et al. |
| 5,249,576 A | 10/1993 | Goldberger et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,387,122 A | 2/1995 | Goldberger et al. |
| D359,546 S | 6/1995 | Savage et al. |
| 5,431,170 A | 7/1995 | Mathews |

(Continued)

FOREIGN PATENT DOCUMENTS

| | | |
|---|---|---|
| AU | 200010929 B2 | 5/2000 |
| CA | 2 346 639 | 4/2000 |

(Continued)

*Primary Examiner* — Eric Winakur

(74) *Attorney, Agent, or Firm* — Knobbe, Martens Olson & Bear LLP

(57) ABSTRACT

A pulse oximetry sensor includes reusable and disposable elements. To assemble the sensor, members of the reusable element are mated with assembly mechanisms of the disposable element. The assembled sensor provides independent movement between the reusable and disposable elements.

12 Claims, 10 Drawing Sheets

(56) References Cited

U.S. PATENT DOCUMENTS

| | | |
|---|---|---|
| D361,840 S | 8/1995 | Savage et al. |
| 5,437,275 A | 8/1995 | Amundsen et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,507,286 A | 4/1996 | Solenberger |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,619,992 A | 4/1997 | Guthrie et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,660,567 A | 8/1997 | Nierlich et al. |
| 5,664,270 A | 9/1997 | Bell et al. |
| 5,673,693 A | 10/1997 | Solenberger |
| 5,678,544 A | 10/1997 | DeLonzor et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,817,008 A | 10/1998 | Rafert et al. |
| 5,817,010 A | 10/1998 | Hibl |
| 5,823,950 A | 10/1998 | Diab et al. |
| 5,830,131 A | 11/1998 | Caro et al. |
| 5,833,618 A | 11/1998 | Caro et al. |
| RE36,000 E | 12/1998 | Swedlow et al. |
| 5,860,919 A | 1/1999 | Kiani-Azarbayjany et al. |
| 5,879,373 A | 3/1999 | Röper et al. |
| 5,890,929 A | 4/1999 | Mills et al. |
| 5,904,654 A | 5/1999 | Wohltmann et al. |
| 5,910,108 A | 6/1999 | Solenberger |
| 5,919,133 A | 7/1999 | Taylor et al. |
| 5,919,134 A | 7/1999 | Diab |
| 5,934,925 A | 8/1999 | Tobler et al. |
| 5,940,182 A | 8/1999 | Lepper, Jr. et al. |
| 5,991,648 A | 11/1999 | Levin |
| 5,995,855 A | 11/1999 | Kiani et al. |
| 5,997,343 A | 12/1999 | Mills et al. |
| 5,999,834 A | 12/1999 | Wang et al. |
| 6,002,952 A | 12/1999 | Diab et al. |
| 6,011,986 A | 1/2000 | Diab et al. |
| 6,014,576 A | 1/2000 | Raley |
| 6,027,452 A | 2/2000 | Flaherty et al. |
| 6,036,642 A | 3/2000 | Diab et al. |
| 6,045,509 A | 4/2000 | Caro et al. |
| 6,061,584 A | 5/2000 | Lovejoy et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,000 B1 | 11/2001 | King |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,381,489 B1 | 4/2002 | Ashibe |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Pishney et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |

(56) References Cited

U.S. PATENT DOCUMENTS

| | | |
|---|---|---|
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |

(56) References Cited

U.S. PATENT DOCUMENTS

| | | |
|---|---|---|
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,224,411 B2 | 7/2012 | Al-Ali et al. |
| 8,228,181 B2 | 7/2012 | Al-Ali |
| 8,229,533 B2 | 7/2012 | Diab et al. |

FOREIGN PATENT DOCUMENTS

| | | |
|---|---|---|
| CA | 2 366 493 A1 | 11/2002 |
| EP | 1 222 894 A2 | 7/2002 |
| EP | 1 222 894 A3 | 7/2002 |
| WO | WO 00/021433 | 4/2000 |
| WO | WO 01/03574 A1 | 1/2001 |

NONINVASIVE OXIMETRY OPTICAL SENSOR INCLUDING DISPOSABLE AND REUSABLE ELEMENTS

RELATED APPLICATIONS

The present application is a continuation of U.S. patent application Ser. No. 11/754,972, filed May 29, 2007, entitled "Noninvasive Oximetry Optical Sensor Including Disposable and Reusable Elements," now U.S. Pat. No. 8,244,325, which is a continuation of U.S. patent application Ser. No. 11/172,587, filed Jun. 30, 2005, entitled "Optical Sensor Including Disposable and Reusable Elements," now U.S. Pat. No. 7,225,007, which is a continuation of U.S. patent application Ser. No. 10/351,645, filed Jan. 24, 2003, entitled "Optical Sensor Including Disposable and Reusable Elements," now U.S. Pat. No. 6,920,345, and claims priority benefit under 35 U.S.C. §120 to the same. The present application incorporates the foregoing disclosures herein by reference.

FIELD OF THE INVENTION

The present invention relates to the field of sensors that measure oxygen content in a patient's blood. More specifically, the invention relates to a sensor that assembles reusable and disposable elements and/or allows longitudinal displacement between the reusable and disposable elements.

BACKGROUND OF THE INVENTION

Early detection of low blood oxygen is important in a wide variety of medical applications, and oximetry was developed to study and to measure, among other things, the oxygen status of blood. One type of oximetry, pulse oximetry, employs a sensor attached to a patient in order to output a signal indicative of a physiological parameter of the patient, such as, for example, the patient's blood oxygen saturation.

A pulse oximeter sensor generally uses a number of sensor components, such as one or more energy emission devices like red and infrared LED emitters, and an energy detection device like a photodiode detector. The sensor is generally attached to a measurement site such as a patient's finger, toe, ear, forehead, foot, hand, heel or the like, using an attachment mechanism such as a disposable tape, reusable housing, Velcro strap, or the like. The attachment mechanism positions the emitter and detector in proximity to the measurement site, such that the emitter projects energy into the blood vessels and capillaries of the measurement site, and the photodiode detector then detects the attenuated energy. The emitted energy can be light or other forms of energy. The detector communicates a signal indicative of the detected attenuated energy to a signal processing device such as an oximeter. The oximeter generally calculates, among other things, one or more physiological parameters of the measurement site.

In sensors where the detector detects emissions through the measurement site, it is generally desirable to position the detector opposite the emitter around the measurement site, such as, for example, above and below a finger. However, sensors are produced in a limited number of sizes and shape configurations, while patients have, for example, fingers and toes of many different sizes and shapes.

In addition, the attachment mechanism and the electronic components of a sensor are generally curved around a measurement site in a manner detrimental to one or more elements of the sensor. For example, the attachment mechanism generally wraps around the measurement site at an approximate "inner circle" having a first radius, while the electronic components such as the flexible circuits are generally fixedly attached to the attachment mechanism. Accordingly, the electronic components can form an approximate "outer circle" having a second radius unequal to the first radius. However, because the attachment mechanism generally does not move independently with respect to the electrical components, attachment of the sensor to the measurement site can exert forces on the electrical components, such as, for example, exerting forces which try to lengthen, or longitudinally stretch the electrical components to account for an increased radius thereof. The forced stretching can damage the electrical components of a flexible circuit, such as the conductive traces.

SUMMARY OF THE INVENTION

Based on the foregoing, embodiments of the present invention include a sensor comprising reusable and disposable sensor elements that permit longitudinal displacement with respect to one another when the sensor is attached to a measurement site. For example, in one embodiment the sensor includes a reusable element and a disposable element configured to receive the reusable element in a releasable attachment assembly providing longitudinal displacement between the disposable and reusable elements. The longitudinal displacement advantageously allows the sensor elements to self-adjust with respect to one another during attachment to the measurement site. The self-adjustment or independent movement advantageously reduces the forces caused by longitudinal stretching, thereby reducing damage to the reusable element.

One aspect of the invention relates to an optical probe including a reusable element and a disposable element that can be attached together by placing or snapping protrusions on one element into apertures and receiving slots on the other element. For example, the reusable element can be fitted with protrusions made of plastic, and the disposable element can be fitted with detents or tabs, which include apertures or receiving slots. The reusable element attaches to the disposable element by inserting, or snapping, the protrusions into the apertures and the receiving slots of the tabs. When assembled, at least some of the protrusions are slidable within the receiving slots to independently move along a longitudinal axis of the sensor, thereby providing some longitudinal decoupling between the reusable element and the disposable element.

Another aspect of the invention relates to a sensor with a reusable element and a disposable element where the reusable element is made of a flexible or pliable material and includes one or more neck sections. The disposable element includes two straps, each of which is configured to receive a neck section. The reusable element and the disposable element are attached together by placing the neck sections within the straps. In one embodiment, the neck sections include a long neck section and a short neck section. The long neck section has a sufficient length to allow longitudinal movement of the reusable element within the strap, thus permitting movement of the reusable element with respect to the disposable element.

Another aspect of the invention relates to a sensor with a reusable element and a disposable element where the reusable element is secured by guides or tabs affixed to the disposable element. The guides allow limited longitudinal motion of the reusable element and thereby allow the reusable element to flex independently of the disposable element as the device is positioned on a patient.

Another aspect of the invention relates to a sensor with a reusable element and a disposable element where the reusable element is encased in a protective cover. In one embodiment, the protective cover is made of a pliable material and prevents any sharp edges from scratching or poking a patient or caregiver. The protective cover also advantageously prevents damage to the reusable element that could occur from dirt, dust, liquids, or other elements of the environment.

Yet another aspect of the invention relates to a sensor with a reusable element and a disposable element where the disposable element includes a breakable element. After an approximate predetermined number of safe uses, the breakable element breaks and the disposable element is rendered inoperable or otherwise indicates its over use.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. The drawings are not necessarily drawn to scale. Throughout the drawings, reference numbers are re-used to indicate correspondence between referenced elements. In addition, the first digit of each reference number indicates the figure in which the element first appears.

DETAILED DESCRIPTION OF THE PREFERRED EMBODIMENT

Figure 1:
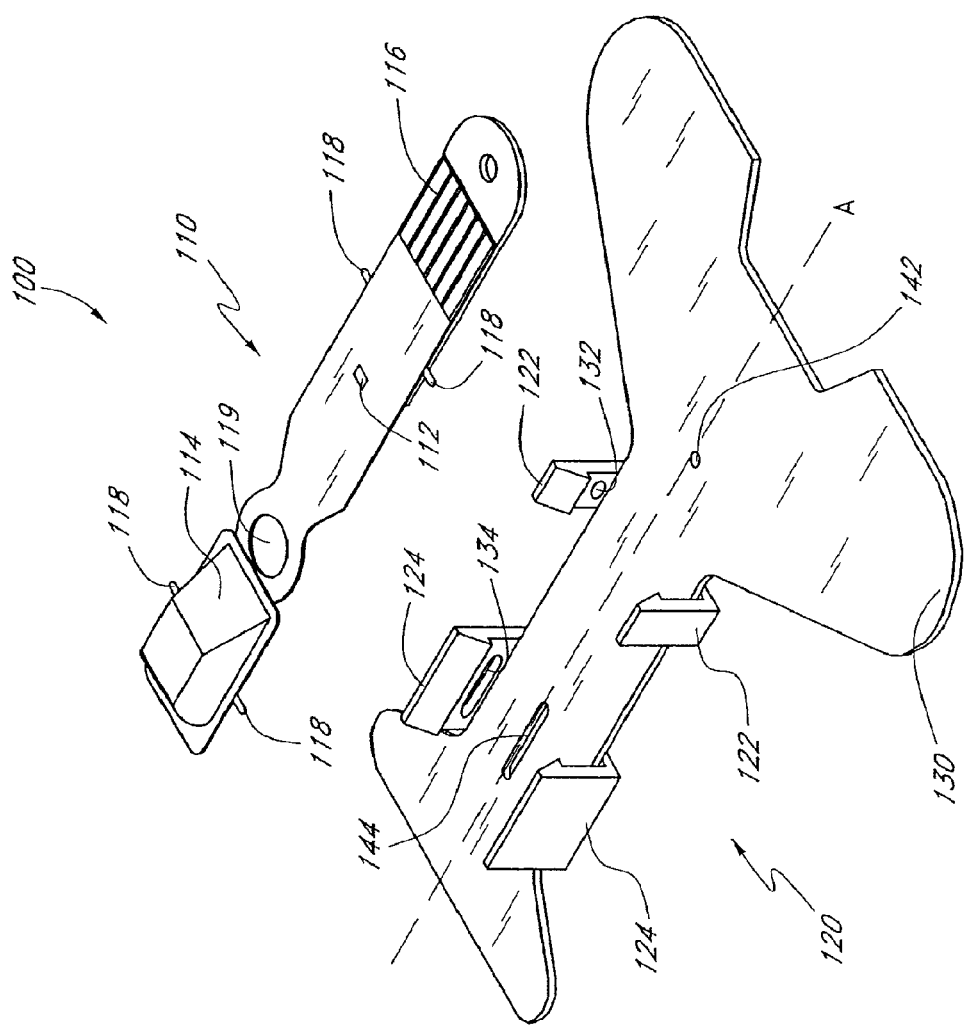
FIG. 1 illustrates a perspective view of an embodiment of an unassembled sensor that includes reusable and disposable elements.

FIG. 1 illustrates an embodiment of a sensor 100. The sensor 100 includes a reusable element 110 and a disposable element 120. According to one embodiment, the reusable element 110 generally includes those components of the sensor 100 that are more expensive, such as, for example, one or more energy emitters, one or more energy detectors, one or more breakable conductors, one or more information elements, some or all of the same, or the like. In addition, the reusable element 110 includes an assembly mechanism generally shaped to mate with a corresponding component of the disposable element 120, as will be disclosed in greater detail below.

The disposable element 120 generally includes those components of the sensor 100 that are less expensive, such as, for example, face tape, bandages, or other mechanisms for removably attaching the reusable element 110 to a measurement site. Moreover, the disposable element 120 includes a mating assembly mechanism generally shaped to mate with assembly mechanism of the reusable element 110, thereby attaching the reusable element 110 to the disposable element 120 in a manner that provides for at least some self adjustment or displacement between the elements.

When the disposable element 120 attaches the reusable element 110 to tissue of a measurement site, a signal processing device, such as an oximeter, activates the energy emitters to transmit light energy into the tissue. The tissue attenuates the light energy, which is then detected by the detector. A signal indicative of the detected light energy is then generally forwarded back to the signal processing device for determination of one or more physiological parameters of the tissue, such as, for example, oxygen saturation, pulse rate, or the like.

A skilled artisan will recognize from the disclosure herein that there are many combinations of differing shapes and circuit configurations for the reusable and disposable elements, 110 and 120, respectively, such as, for example, those disclosed in U.S. Pat. No. 6,377,829, and U.S. patent application Ser. No. 10/020,664, filed on Dec. 11, 2001, both of which are hereby incorporated by reference.

As shown in the exemplary embodiment of FIG. 1, the reusable element 110 can include one or more energy emitters 112, an energy detector 114, and an electrical connector 116 electrically communicating with the emitters 112 and the detector 114 through a flexible circuit. According to one embodiment, the flexible circuit comprises material of a generally flexible or pliable construction.

The reusable element 110 also includes the foregoing assembly mechanism, such as, for example, the one or more protrusions 118. According to one embodiment, the protrusions 118 comprise approximately cylindrical-shaped or tab-shaped extensions made of plastic or other durable materials. FIG. 1, shows the reusable element 110 including four protrusions 118, two opposing protrusions proximate a front portion and extending in opposite generally horizontal directions, and two opposing protrusions proximate a back portion and extending in opposite generally horizontal directions. According to one embodiment, the protrusions 118 roughly align with one or more of the electronic components of the sensor 100. As described below, the protrusions 118 each advantageously mate with the mating assembly mechanism of the disposable element 120 in a manner providing for at least some displacement of the reusable element 110 with respect to the disposable element 120, thereby avoiding damage or harmful wear of the reusable element 110.

FIG. 1 also shows the flexible circuit including an optical barrier, such as, for example, an aperture or gap 119 to reduce light energy from traveling from the emitter 112 to the detector 114 without first passing through tissue at the measurement site (i.e., light piping). A skilled artisan will recognize from the disclosure herein that the gap 119 could be replaced with opaque materials, protrusions, pads, tabs, or other light blocking mechanisms.

Although disclosed with reference to preferred embodiments, a skilled artisan will recognize from the disclosure herein, a number of other embodiments of the reusable element 110. For example, one or more of the emitters 112 or the detector 114 can be located on the disposable element 120. Moreover, the flexible circuit may comprise plastic, electric wires, polyester substrates, or the like.

FIG. 1 also shows the disposable element 120. According to an embodiment, the disposable elemental 120 generally comprises a base 130 comprising a face tapestock material similar to that of an adhesive bandage shaped to position the reusable elemental proximate the measurement site. The face tape can include an adhesive covered base protected by one or more conveniently shaped release liners or layers. Although illustrated in a conventional elongated surface with opposing wings style shape, an artisan will recognize from the disclosure herein that the tape may comprise virtually any shape, including those disclosed in U.S. patent application Ser. No. 10/020,664, referenced above. Moreover, the disposable elemental 120 may comprise a Velcro strap, a foam wrap, a reusable plastic housing or the like.

The disposable element 120 also includes the assembly mechanism, illustrated as tabs 122 and 124. Each of the tabs 122 include an aperture 132, while each of the tabs 124 include a receiving slot 134. In one embodiment, the apertures 132 and the receiving slots 134 have sufficient depth to receive the protrusions 118. In other embodiments, the apertures 132 and receiving slots 134 extend through the tabs 122 and 124. As shown in FIG. 1, the tabs 122 and 124 are shaped to removably receive the reusable elemental 110. For example, the tabs 122 and 124 can include sloped surfaces that cause the tabs 122 and 124 to displace outwardly during assembly of the sensor 100. For example, when the reusable element 110 is properly positioned within the tabs 122 and 124, the tabs 122 and 124 snap inwardly over the reusable element 110 such that the protrusions 118 are within the apertures 132 and the receiving slots 134. When assembled, vertical and horizontal movement between the reusable and disposable elements, 110 and 120 respectively, is substantially prevented by the relationship between the tabs 122 and 124, the apertures 132, the slots 134 and the protrusions 118. However, the slots 134 provide for displacement between elements along longitudinal axis A when the disposable portion 120 is wrapped around a measurement site by allowing the protrusions 118 to slide back and forth within the slots 134. Thus, the assembly mechanisms of the reusable and disposable elements, 110 and 120, provide independent movement between the elements, thereby allowing self-adjustment of the sensor 100 to the differing radiuses of each element. Such construction advantageously reduces the harmful stressing effects applied to components of the reusable element 110.

FIG. 1 also shows that a gap 142, slot or aperture, or otherwise transparent area can be included on the disposable element 120 to permit light from the emitter 112 to travel through the disposable element 120 to the tissue of the measurement site. Moreover, another gap 144 can be included on the disposable element 120 to permit attenuated light from the measurement site tissue to travel through the disposable element 120 to the detector 114. In another embodiment, some or all of the base 130 of the disposable element 120 is made of a transparent material, and the gaps 142 and 144 can be omitted.

A skilled artisan will recognize from the disclosure herein that the tabs 122 and 124 of the disposable element 120 can be implemented in a wide variety of embodiments. For example, an embodiment can include each of the tabs 122 and 124 having a receiving slot 134 while another embodiment can include each of the tabs 122 and 124 having an aperture 132.

Figure 2:
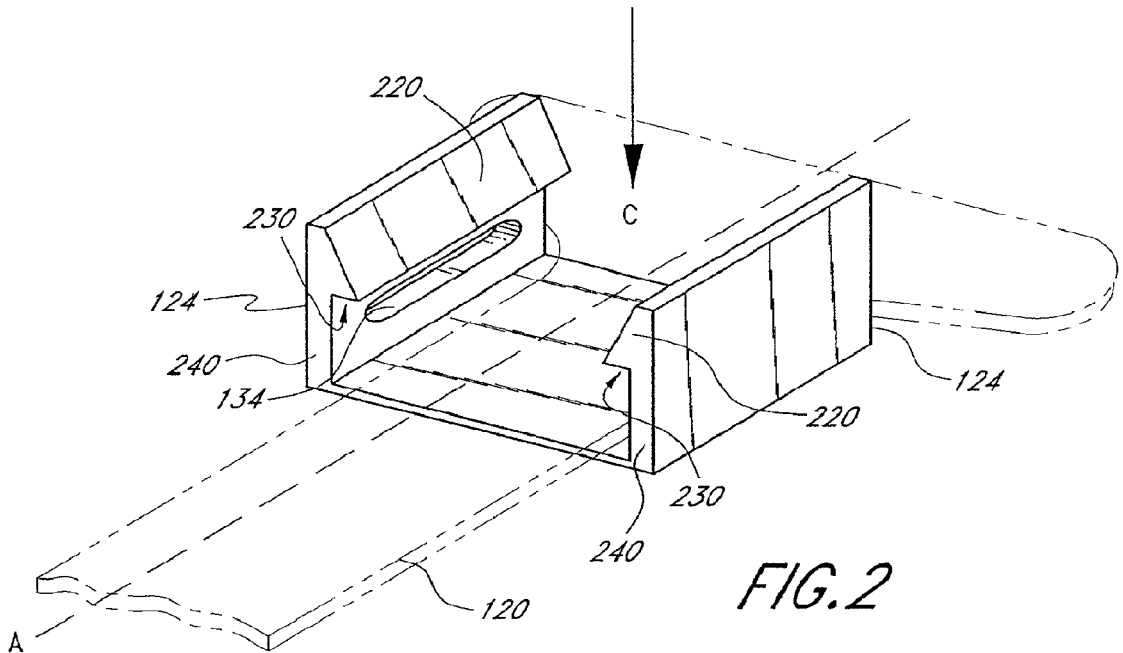
FIG. 2 illustrates a perspective view of tabs of the disposable element of FIG. 1.

FIG. 2 illustrates a perspective view of the tabs 124 including the receiving slots 134. As disclosed, the tabs 124 can be shaped to include a sloped surface 220 configured to displace a ledge or catch 230 during sensor assembly. For example, the sloped surface 220 displaces outwardly when protrusions 118 are pressed in the direction of the arrow C. Then when the reusable element 110 is properly positioned, the protrusions 118 snap into the receiving slots 134 and the catch 230 snaps over a top surface of the reusable element 110.

The receiving slots 134 are longer than the cross sectional width of the protrusions 118 so that the protrusions 118 can move within the receiving slots 134 to different positions along the longitudinal axis A of the disposable element 120. The apertures 132, on the other hand, are sized to allow protrusions 118 to be located within the apertures 132 but to prevent substantial movement along the longitudinal axis A of the disposable element 120, thus ensuring proper positioning of the sensor elements, with respect to the tissue and one another.

In an embodiment, the reusable element 110 and the disposable element 120 are assembled into the sensor 100 when the protrusions 118 are snapped into the apertures 132 and the receiving slots 134 of the tabs 122 and 124. The assembled sensor 100 is then attached to a measurement site, through, for example, application of the adhesive covered side of the face tape to tissue at the measurement site. During application, the protrusions 118 within the receiving slots 134 move along the receiving slot 134, while the protrusions 118 remain positioned within the aperture 132. This type of flexibility advantageously reduces the stretching force placed on conventional reusable elements.

FIG. 2 also shows receiving slots 134 as grooves in the walls 240 of the tabs 124, where the grooves do not extend all the way through the walls 240. In other embodiments, the receiving slots 134 can be open slots that extend through the walls 240. Likewise, the aperture 132 can be straightforward depressions, or punch through holes.

Figure 3A:
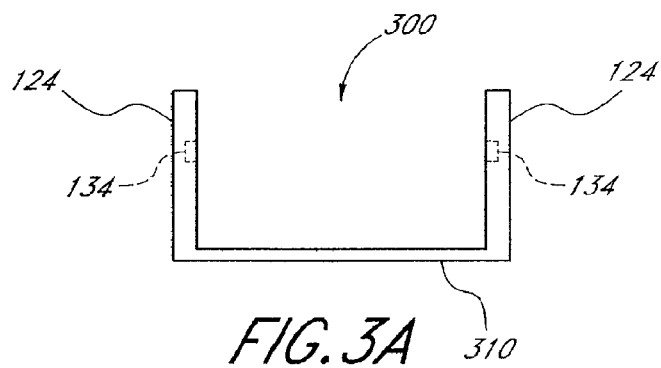
FIG. 3A illustrates a cross-sectional view of another embodiment of tabs of a disposable element.

FIG. 3A illustrates a cross-sectional view of tabs 300 of another embodiment of a disposable element, such as disposable element 120 of FIG. 1. The tabs 300 include the receiving slot 134 for receiving the protrusions 118, but does not include the sloped surface 220 or the catch 230 of FIG. 2. Thus, the reusable element 110 is assembled relying on the interaction described in the foregoing between the protrusions 118 and the apertures 132 and the slots 134.

Figure 3B:
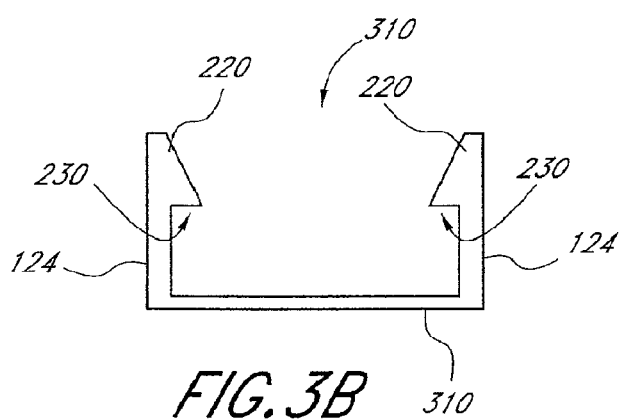
FIG. 3B illustrates a cross-sectional view of yet another embodiment of tabs of a disposable element.

FIG. 3B illustrates a cross-sectional view of tabs 310 of another embodiment of a disposable element, such as the disposable element of FIG. 1. The tabs 310 include the sloped surface 220 and the catch 230, but do not include the receiving slot 134 or aperture 132. Thus, the sensor 100 is assembled relying on the interaction between the catch 230 and the surface of the reusable element 110.

Figure 4A:
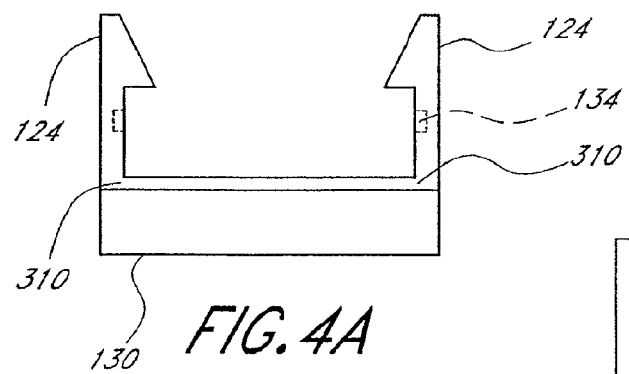
FIG. 4A illustrates a cross-sectional view of the two tabs of FIG. 2, adhesively attached to the disposable element.

FIG. 4A illustrates a cross-sectional view of the tabs 124 of FIG. 1 adhesively attached to the disposable element 120, according to an embodiment. In FIG. 4A, the tabs 124 are attached to the base 130 by adhesive. In a preferred arrangement, the tabs 124 share a common substrate 310, and an adhesive is applied between the substrate 310 and the base 130 to attach the tabs 124 to the disposable element 120.

Figure 4B:
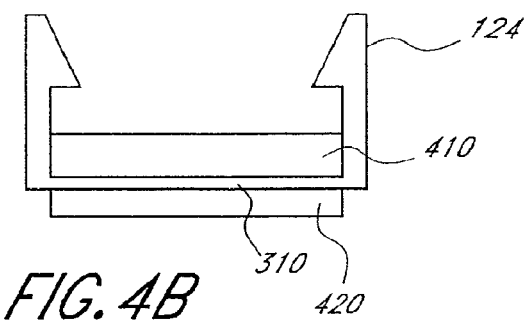
FIG. 4B illustrates a cross-sectional view of the two tabs of FIG. 2, attached between layers of the disposable element.

FIG. 4B illustrates a cross-sectional view of the tabs 124 of FIG. 1 attached between layers of the disposable element 120 of FIG. 1, according to another embodiment. In FIG. 4B, the tabs 124 are attached between two layers 410 and 420 of the base 130. In a preferred arrangement, the two tabs 124 share a common substrate 310, and the substrate 310 is sandwiched between the layers 410 and 420.

A skilled artisan will recognize from the disclosure herein that the embodiments disclosed with reference to FIGS. 3 and 4 can be applied to one or both sets of the tabs 122 and 124. Moreover, a skilled artisan will recognize from the disclosure herein that the protrusions 118 can be attached to the reusable element 110 in a number of ways, such as, for example, attached by adhesive to the reusable element 110, manufactured as integral parts of the reusable element 110, sandwiched between a top layer and a bottom layer of the reusable element 110, or the like.

Figure 5:
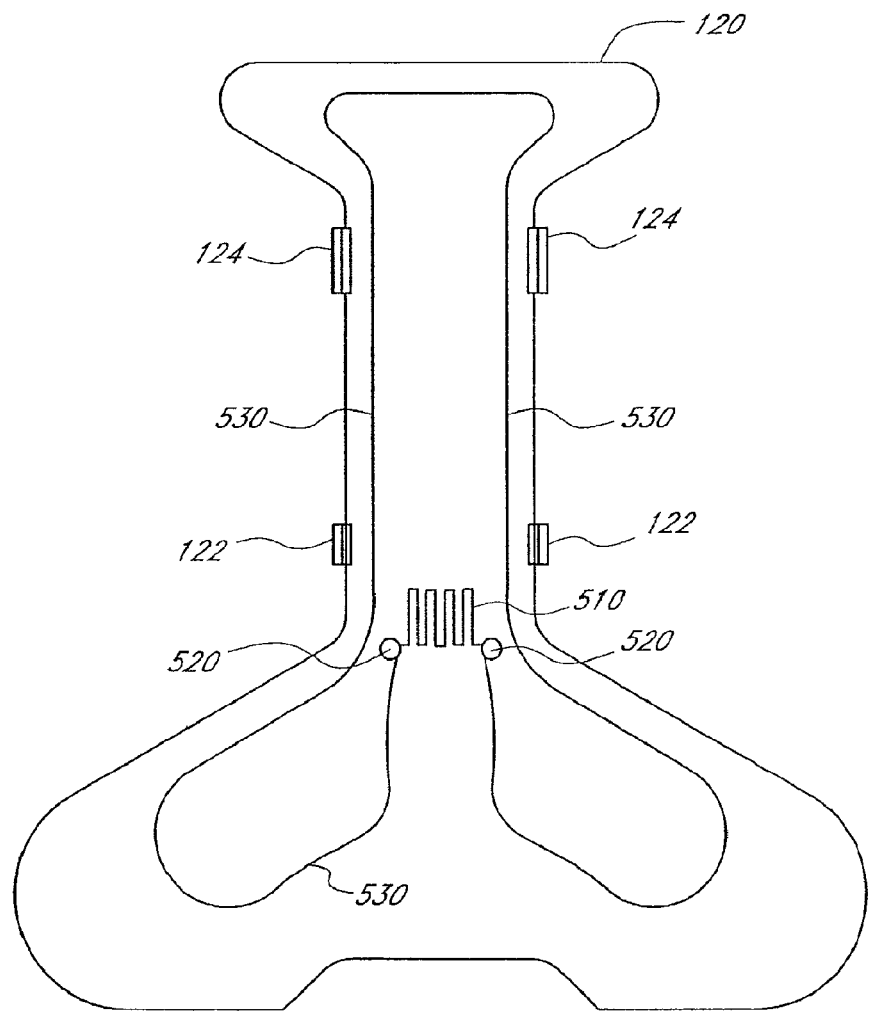
FIG. 5 illustrates a top view of the disposable element of FIG. 1, including an information element and breakable conductor.

FIG. 5 illustrates a top view of the disposable element of FIG. 1, including an information element 510, contacts 520, and a breakable conductor 530, according to yet another embodiment. The contacts 520 can electrically connect with contacts on the flexible circuit of the reusable element 120, thereby adding the information element 510 and/or the breakable conductor 530 into the electric circuit of the sensor 100. As is understood in the art, the information element 510 can provide an indication of the sensor or patient type, operating characteristics or the like, or that the sensor 100 is from an authorized supplier. In an embodiment, the information element 510 is a resistive element made by depositing a conductive ink trace having a predetermined length and width. The information element 510 is disposed between contacts 520, which can also be implemented with conductive ink. As an artisan will recognize from the disclosure herein, many type of information elements can be included, such as, for example, passive or active elements, accessible memory elements, or the like.

The breakable conductor 530 is configured to break after a predetermined number of safe uses, thus providing quality control to ensure that the disposable element 120 is not over used. Various embodiments of information element 510, contacts 520, and breakable conductor 530 can be found in U.S. Pat. No. 6,377,829.

Figure 6:
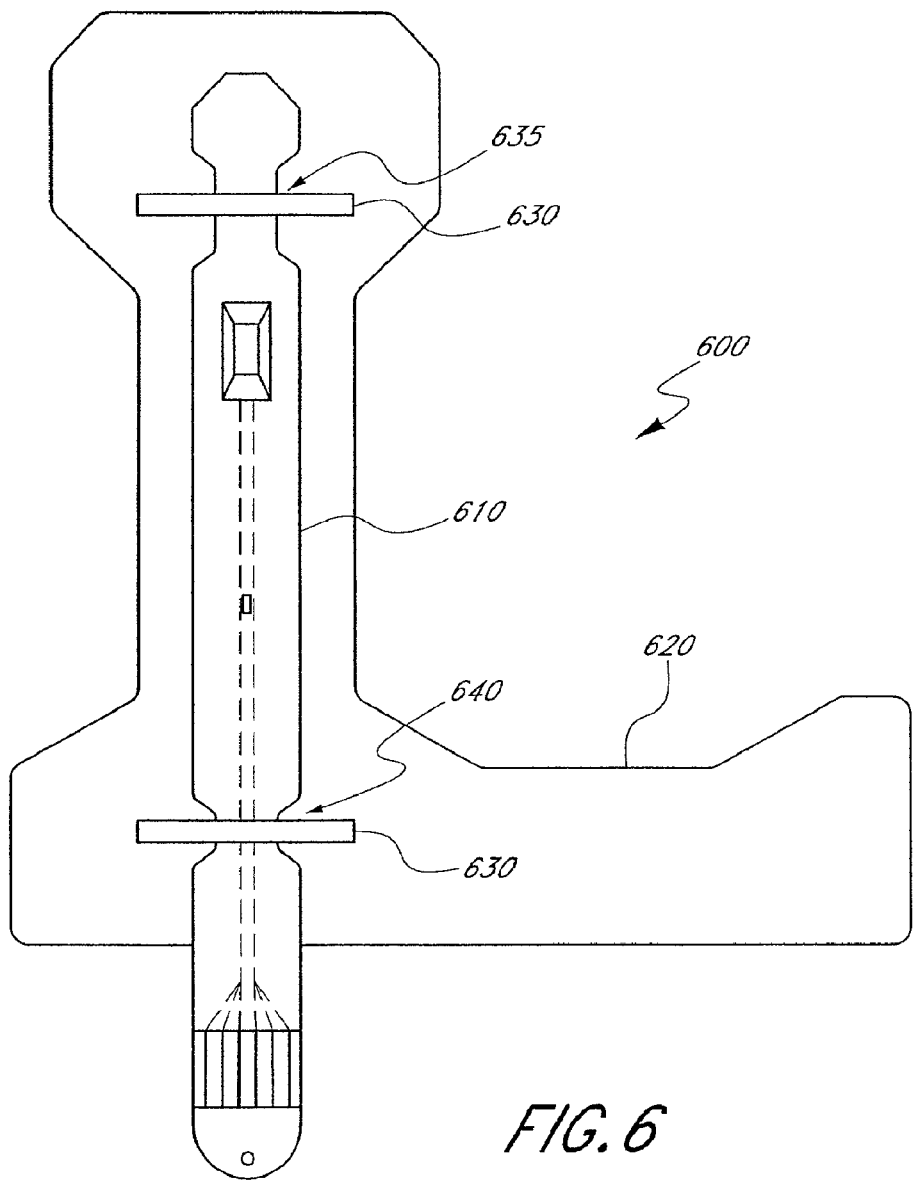
FIG. 6 illustrates a top view of another embodiment of an assembled sensor that includes reusable and disposable elements.

FIG. 6 illustrates a top view of an assembled sensor 600 that includes reusable and disposable elements, according to another embodiment. As shown in FIG. 6, the sensor 600 includes a reusable element 610 and a disposable element 620. The disposable element 620 includes straps 630 which position the reusable element 610 as described below. As shown in FIG. 6, the reusable element 610 can be similar to the reusable element 110 of the foregoing embodiments, generally including, for example, the more expensive components of the sensor 600. Moreover, disposable element 620 can be similar to the disposable element 120 of the foregoing embodiments, generally including for example, a disposable tape. The disposable tape can be virtually any suitable shape, and is shown in FIG. 6 in a generally "L" shaped configuration.

FIG. 6 also shows the reusable portion 610 including an extended narrow neck or notch 635 and a neck or notch 640, each narrower in width than the general width of the reusable element 610. The straps 630 attached to the disposable element 620 extend over the necks 635 and 640 to position the reusable element 610 with respect to and proximate the disposable element 620. The straps 630 provide for longitudinal movement between the elements of the sensor 600 similar to that disclosed in the foregoing.

Figure 7A:
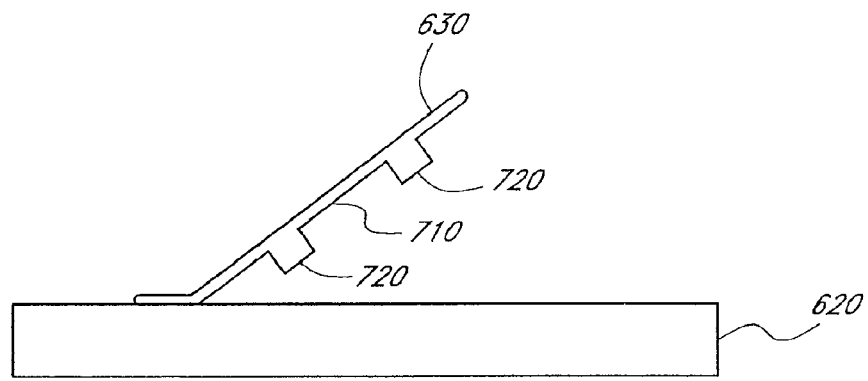
FIGS. 7A and 7B illustrate simplified cross-sectional views of an embodiment of a strap of the disposable element of FIG. 6.
Figure 7B:
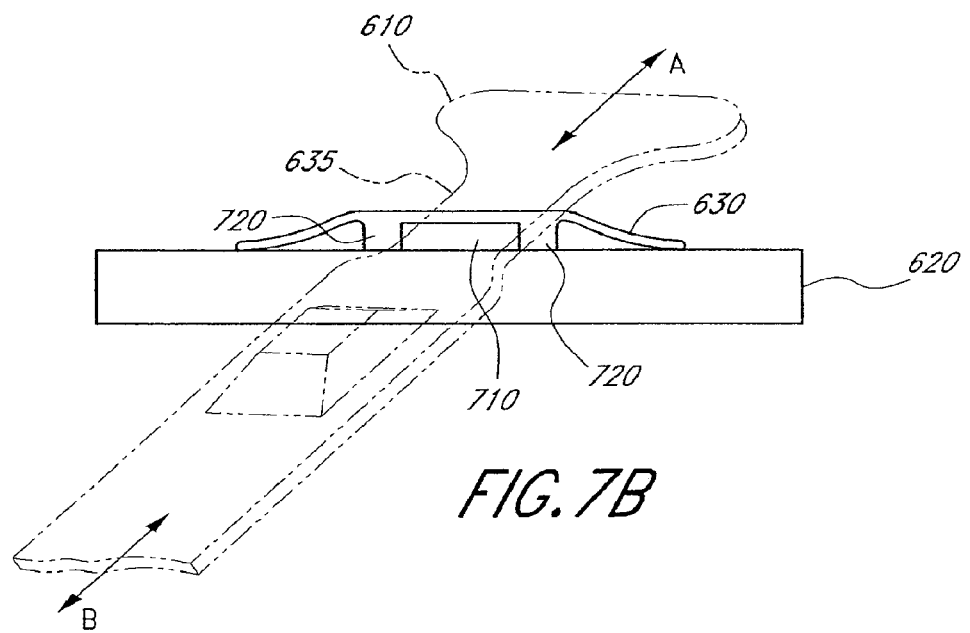

FIG. 7A illustrates a simplified cross-sectional view of one of the straps 630 of the disposable element 620 of FIG. 6, according to an embodiment. The strap 630 may comprise a hook-and-loop device such as Velcro. The strap 630 may alternatively be an integral part of the structure of the disposable element 620. According to an embodiment, the strap 630 includes blocks 720 forming a gap 710 therebetween. As shown in FIG. 7A, an embodiment of the strap 620 can be removed from the disposable element 620 to permit the neck 630 of the reusable element 610 to be placed within the gap 710, as show in FIG. 7B an artisan will also recognize from the disclosure herein that the pliable material of the reusable portion 610 can alternatively or concurrently be compressed together and guided through attached straps 630.

According to one embodiment, the gap 710 is as wide or slightly wider than the necks 635 and 640, but narrower than other adjacent portions of the reusable element 610. Therefore, once placed in the gaps 710 and attached to the disposable element 620, the reusable element 610 can be moved along its longitudinal axis along the arrows A and B (FIG. 7B), but only to the extent that the necks 635 and 640 remain in the gaps 710.

In one embodiment shown in FIG. 6, the reusable element 610 includes the relatively "long" neck 635 shown near the top of the figure and a relatively "short" neck 640 shown near the bottom of the figure. Once the two necks 635 and 640 are placed within the straps 650, the long neck 635 allows the reusable element 610 to be moved along a longitudinal axis of the disposable element 120. In contrast, the short neck 640 prevents substantial movement along the longitudinal axis. Thus, similar to embodiments disclosed in the foregoing, the sensor 600 allows the neck 630 to self adjust during application to a measurement site, thereby avoiding damaging the reusable element 610.

Figure 8:
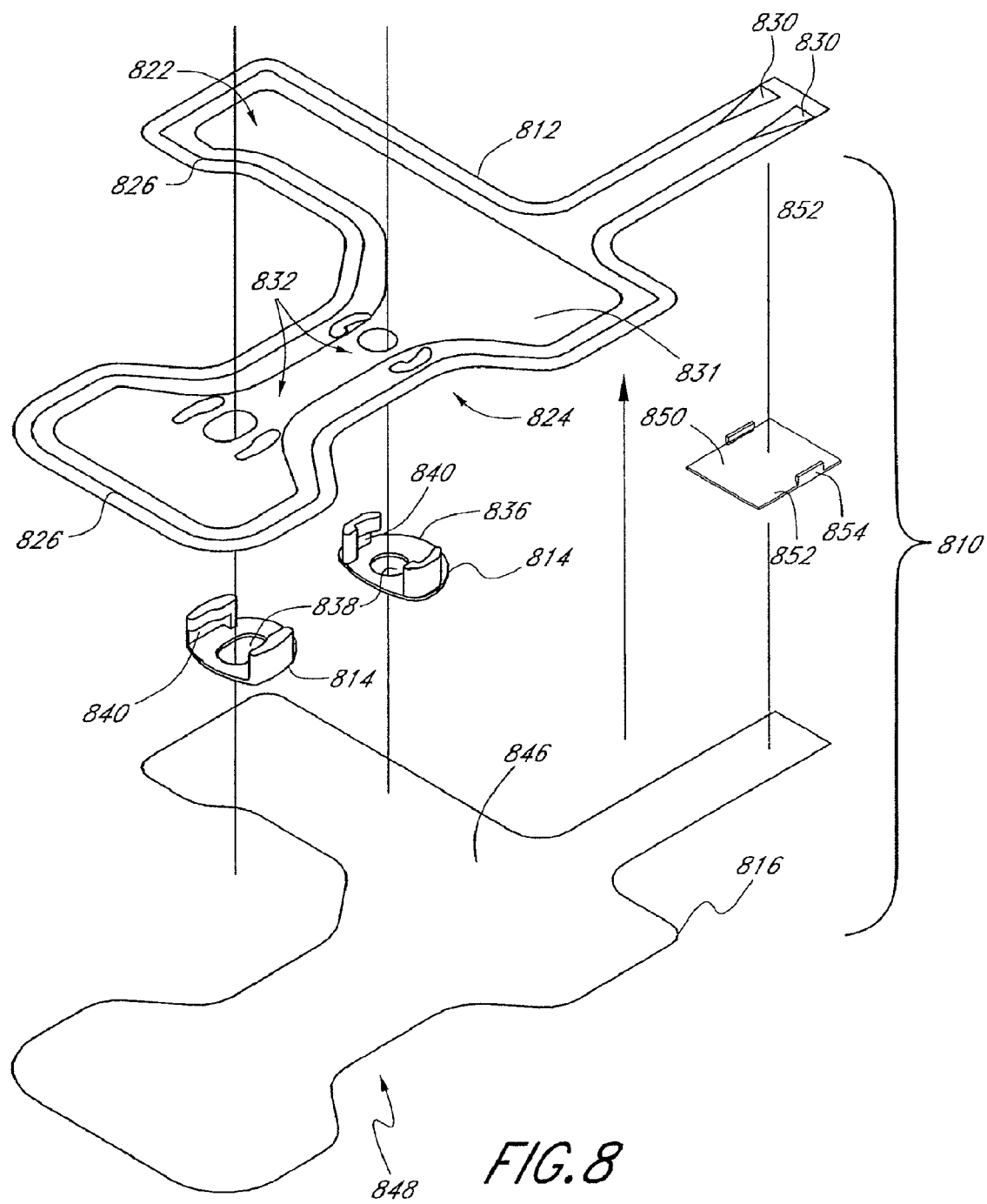
FIG. 8 illustrates an exploded view of a disposable element according to another embodiment of an optical sensor.

FIG. 8 illustrates an exploded view of a disposable element 810 according to another embodiment of an optical sensor. The disposable element 810 includes a top layer 812, at least one attachment mechanism, tab, or positioning guide 814, and an adhesive, preferably transparent, tape layer 816. FIG. 8 shows tabs 814 positioned in a back-to-back or opposing manner, as will be described in greater detail below.

FIG. 8 shows the top layer 812 as a generally L shaped tape or other pliable substrate including a first side 822 and a second side 824, although an artisan will recognize from the disclosure herein that the virtually any shape can be used which provides attachment to tissue of a patient. According to an embodiment, the first side 822 includes a breakable element 826, such as the conductive trace disclosed in U.S. Pat. No. 6,377,829, discussed in the foregoing. The breakable element 826 is included into the electrical circuit of the optical sensor through electrical leads or contacts 830 configured to electrically communicate with contacts of a reusable element of the optical sensor. Moreover, the first side 822 of the top layer 812 can optionally include an optical barrier layer 831, such as a layer of material opaque or substantially opaque to light. The optical barrier layer 831 is generally designed to help prevent ambient light or light piping from interfering with the optical signals before or after they are passed through the tissue of the patient. In one embodiment, the barrier layer 831 comprises conductive trace material similar to that of the breakable element 826.

According to an embodiment, the top layer 812 also includes a plurality of apertures 832, which when the optical sensor is assembled, accept portions of the tabs 814 in a manner designed to provide proper placement, positioning, and support of the tabs 814. However, an artisan will recognize from the disclosure herein that top layer 812 may use ink outlines combined with adhesive, or the like to help an assembler properly place and support the tabs 814 on the first side 822 of the top layer 812.

Each tab 814 includes a base 836, a signal aperture 838, and grooves or slots 840. The base 836 connects and supports each of two raised side members forming a generally U shaped structure. The signal apertures 838 comprise holes through which a properly positioned sensor element can emit or detect optical signals, and the raised side members each include the slot 840, similar to the grooves 134 of the tabs 124 of FIG. 1. However, unlike FIG. 1, an embodiment of each of the slots 840 opens from one side of the raised side member, extends along the side member, and ends before the other side of the raised side member. Thus, the slot 840 accepts a protrusion or the like from an insertion side, and allows the protrusion to slide within the slot 840 to the end thereof, proximate a blocked side. Moreover, according to one embodiment, the blocked sides of the tabs 814 approximately adjacently oppose one another, such that protrusions inserted into the insertion sides, are at one point blocked from sliding closer than a predetermined distance from one another by the blocked sides.

According to one embodiment, the tape layer 816 comprises a transparent tape or other substrate layer. The tape layer 816 has a first side 846 and a second side 848. When assembled, the first side 846 adheres to the top layer 812 and sandwiches the tabs 814 therebetween. The second side 848 includes an adhesive, hook-and-loop, similar or combination structure configured to secure the disposable element 810 to tissue of a patient.

FIG. 8 also shows the disposable element 810 including a cable connector 850. The cable connector 850 generally provides for connection of the disposable element 810 to the remainder of a sensor, such as, for example, the reusable elements. According to the exemplary embodiment, the cable connector 850 comprises a plastic plate 852 including mating portions 854, such as, for example, raised pliable detents that each including a catch. However, an artisan will recognize from the disclosure herein any suitable mating mechanism can be used to connect the disposable element 810, including virtually any mechanical-type mating mechanism, adhesives, hook-and-loop materials, combinations, or the like.

Figure 9:
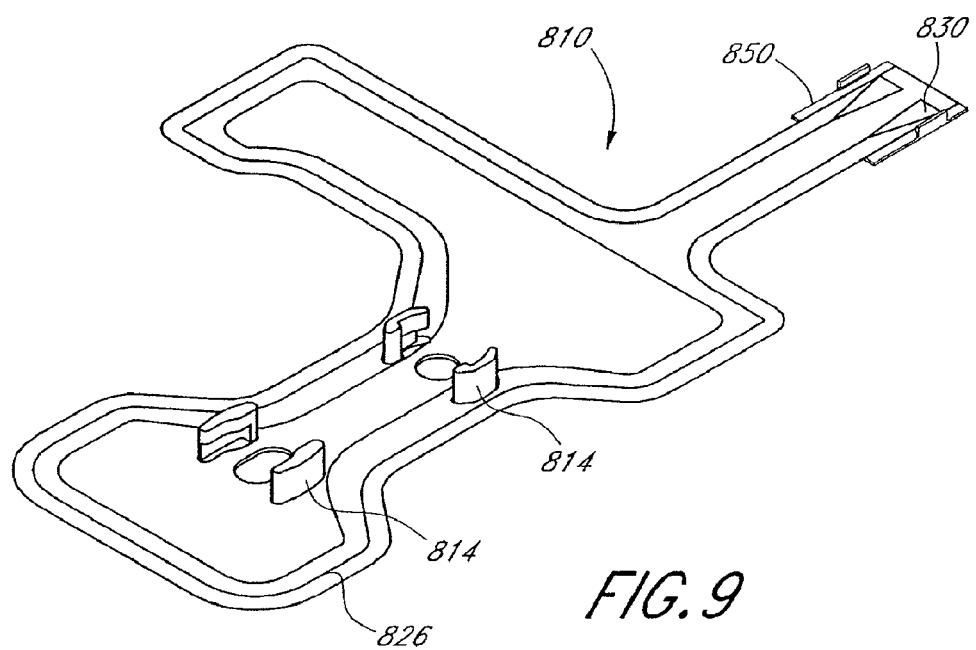
FIG. 9 illustrates a perspective view of the disposable element of FIG. 8.

When the disposable element 810 is assembled as shown in FIG. 9, the bases 836 of the tabs 814 and the plate 852 communicate with the second side 824 of the top layer 812 and first side 846 of the tape layer 816 such that the bases 836 of the tabs 814 and the plate 852 are secured in position between the top layer 812 and the tape layer 816. The raised side members of the tabs 814 extend through the plurality of apertures 832 in the top layer 812, thereby aligning the signal apertures 838 with apertures in the top layer 812. Moreover, as shown in the illustrated embodiment, the mating portions 854 of the cable connector 850 extend above the top layer 812.

Figure 10:
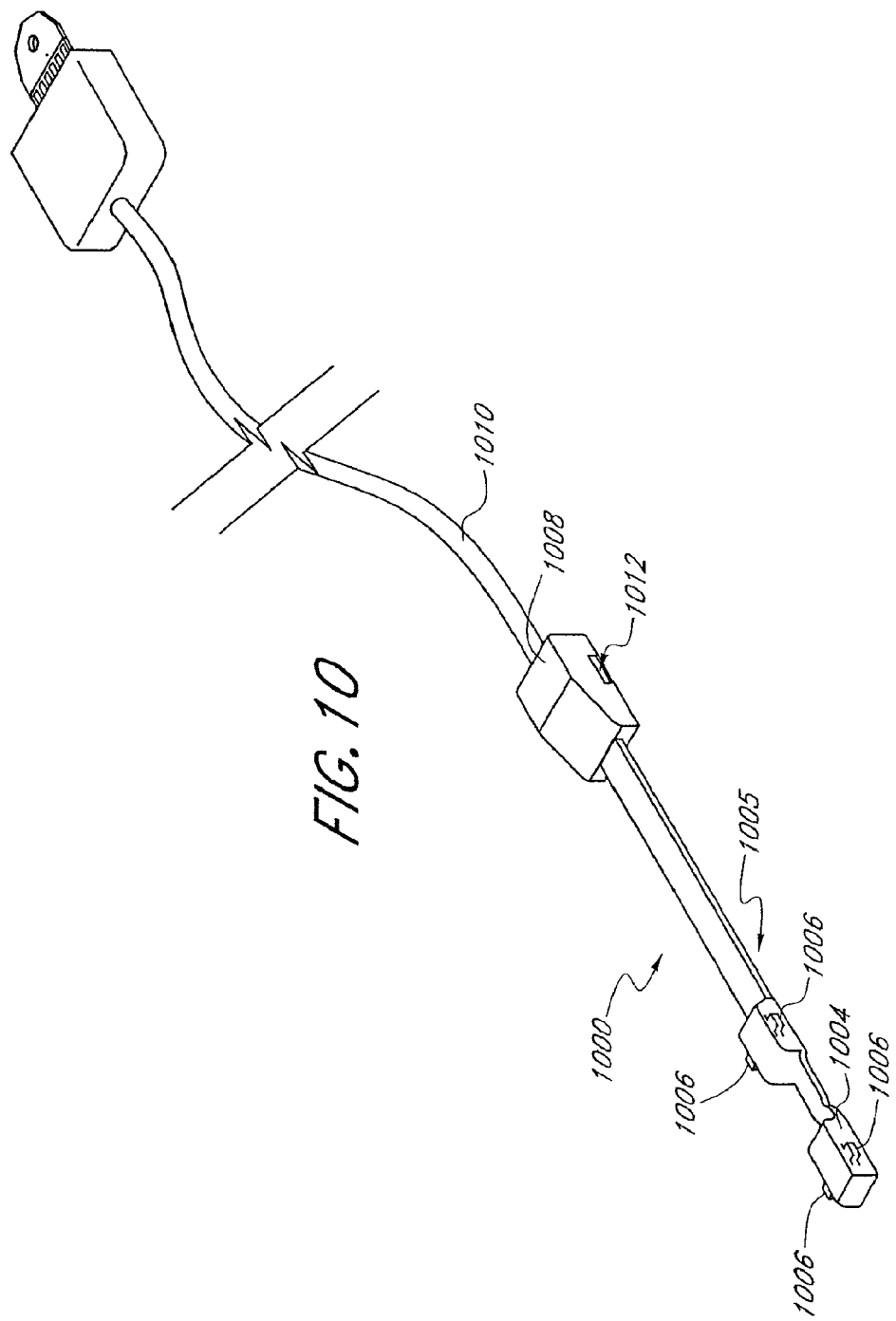
FIG. 10 illustrates a perspective view of an embodiment of a reusable element according to an embodiment of the optical sensor of FIG. 8.

FIG. 10 shows a perspective view of an embodiment of a reusable element 1000. The reusable element 1000 preferably includes a protective cover or coating 1004 covering a plurality of electronic sensor elements 1005 and a plurality of protrusions 1006. The reusable element 1000 also includes a cable connection housing 1008, and cord or cable 1010. According to one embodiment, the protective cover 1004 comprises a soft material, such as a pliable rubber, plastic or the like, which preferably encapsulates and protects the electronic sensor elements 1005 from damage and advantageously protects caregivers and patients from sharp corners often associated with the reusable element 1000, such as, for example, the protrusions 1006 or the sensor elements 1005.

Figure 12:
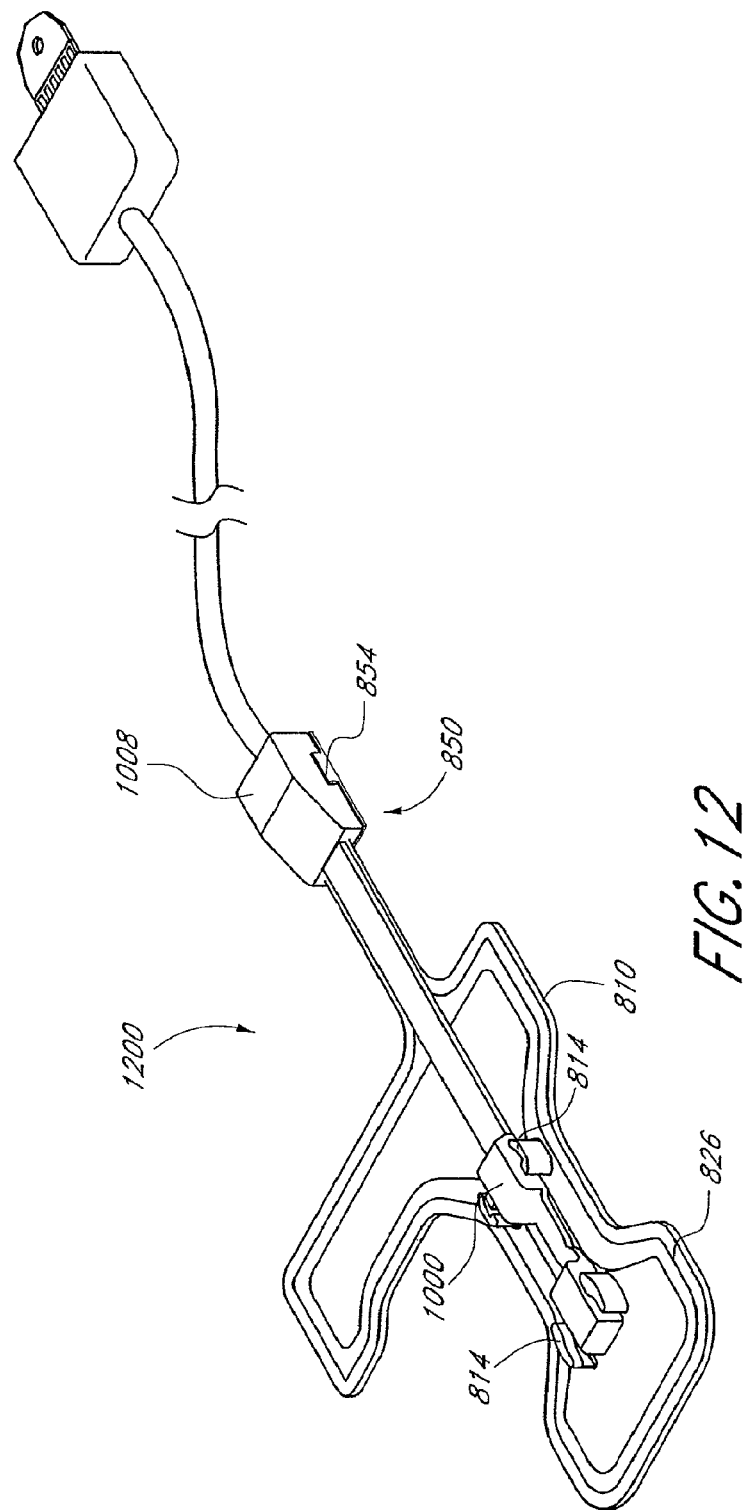
FIG. 12 illustrates a perspective view of the assembled optical sensor including the disposable element of FIG. 8 and the reusable element of FIG. 10.

The protrusions 1006 extend from opposing sides of the reusable element 1000 in generally horizontal and opposing directions. To assemble the optical sensor, the protrusions are aligned with the outside-facing insertion side of each of the slots 840 of the disposable element 810, shown in FIG. 8, and are slid toward one another on each side. As can be seen in FIG. 12, an embodiment of the assembled sensor includes one or more of the protrusions 1006 abutting the blocked side of one pair of the slots 810, while the other protrusions 1006 are proximate the blocked side of the other pair of slots 810, thereby allowing the reusable element 1000 to self adjust and avoid the detrimental stretching forces caused from application to a measurement site.

FIG. 10 also shows the cable connection housing 1008 including insertion slots 1012 configured to receive and mate with the mating portions 854 of the cable connector 850 shown in FIG. 8. When mated, the cable connection housing 1008 provides electrical contact between the electrical leads 830 of the disposable element 810 and the sensor circuitry.

Figure 11:
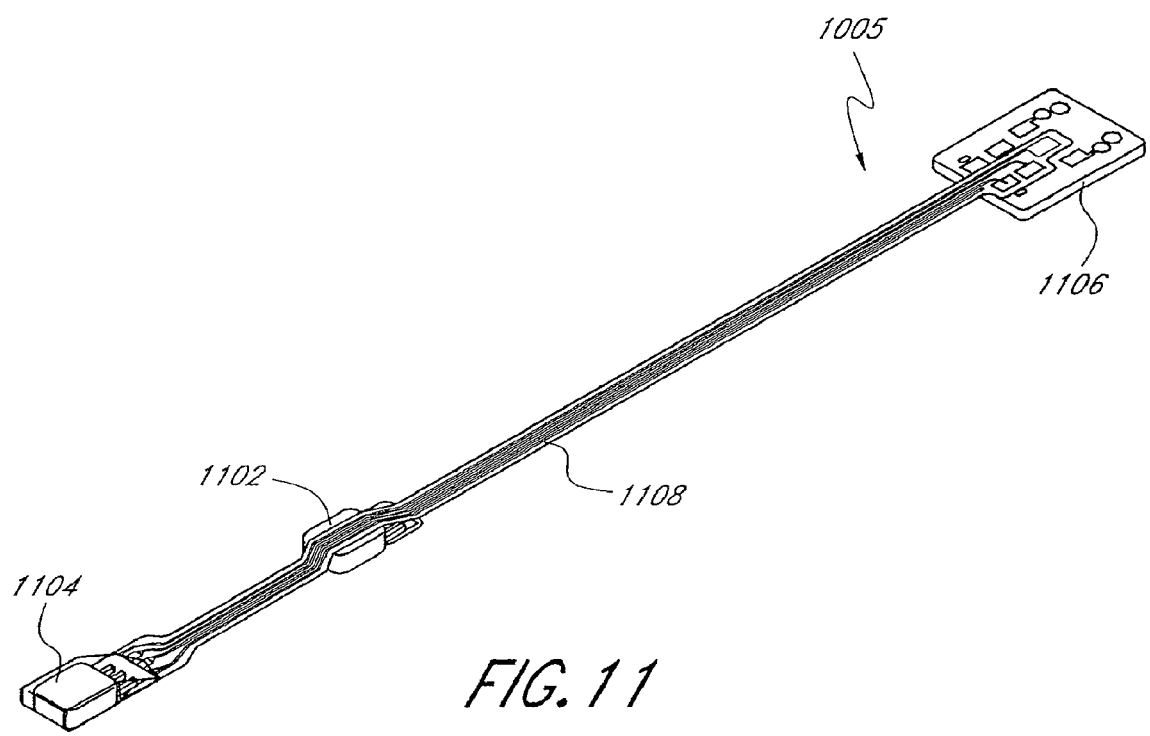
FIG. 11 illustrates a perspective view of a flex circuit of the reusable element of FIG. 10.

FIG. 11 illustrates a perspective view of portions of the electronic sensor elements 1005 of the reusable element 1100 without the protective cover or coating 1004. The elements 1005 include one or more energy emitters 1102, such as one or more LEDs, an energy detector 1104, such as a photodetector, electrically connected to a connector 1106 through a flexible circuit 1108. The connector 1106 is configured to electrically communicate with the leads 830 of the disposable element 810 when the sensor is assembled. Moreover, the connector 1106 is configured to electrically attach the conductive traces of the flexible circuit 1108 to the conductors of the cable 1010.

FIG. 12 shows a perspective view of an assembled sensor 1200. The sensor 1200 includes the reusable element 1000, including the disposable element 810 connected to the connection housing 1008 through the mating portions 854 of the cable connector 850, such that the breakable element 826 is part of the electrical circuitry of the sensor. In one embodiment, the sensor is inoperative or otherwise provides an indication of overuse or misuse when the breakable element 826 is broken or otherwise becomes an open circuit.

As disclosed, when connected to the disposable element 810, the protrusions 1006 have a limited range of motion within the tabs 814, thereby giving the reusable element 1000 a limited range of longitudinal motion independent of the disposable element 810. As described with other embodiments, this longitudinal motion allows the disposable element 810 and the reusable element 1000 to flex independently as the sensor 1200 is attached to tissue of a user, such as a finger, toe, ear, or the like, thereby avoiding damage or unnecessarily harmful wear of the reusable element 1000. Also, this limited range of motion ensures at least approximate proper alignment of various sensor components.

After use, as with embodiments described above, the disposable element 810 is removed and discarded, while the reusable element 812 can be sterilized and reused.

Although the foregoing invention has been described in terms of certain preferred embodiments, other embodiments will be apparent to those of ordinary skill in the art from the disclosure herein. For example, although the above sections describe a reusable element fitted with protrusions or necks and a disposable element fitted with apertures and receiving slots or straps, the embodiments can be reversed having, for example, the reusable element fitted with the apertures, receiving slots, or straps, and with the disposable element fitted with the protrusions or necks.

Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

What is claimed is:

1. A noninvasive optical oximetry sensor, the sensor when assembled configured to attach to a measurement site of a monitored patient and to output signals responsive to light absorption by tissue at said measurement site, said signals including sufficient information for an oximeter to determine one or more physiological parameters of the patient including at least one of oxygen saturation or pulse rate, the oximetry sensor comprising:
   a disposable portion including slots; and
   a reusable portion including:
      a flex circuit;
      a light source;
      one or more detectors configured to detect light from said light source after attenuation by said tissue and output said signals responsive to said detected light;
      a plurality of conductors proximate said flex circuit, some of said conductors communicating with said light source and others of said conductors communicating with said one or more detectors;
      a protective coating encasing at least said light source, said one or more detectors and at least some of said conductors and some of said flex circuit; and
      tabs proximate at least said light source and said one or more detectors,
   wherein said tabs are configured to mate with said slots of said disposable portion where at least some of said slots are shaped to allow said tabs to move within said mated slots to self-adjust the disposable portion and the reusable portion with respect to one another when the disposable portion is applied to said patient after sensor assembly.

2. The noninvasive optical oximetry sensor of claim 1 wherein said protective coating comprises a flexible protective coating.

3. The noninvasive optical oximetry sensor of claim 2 wherein the flexible protective coating comprise a rubber or plastic material.

4. The noninvasive optical oximetry sensor of claim 1, wherein said protective coating includes apertures providing a light path from said light source or said detector to said measurement site.

5. The noninvasive optical oximetry sensor of claim 1, wherein said at least some of said slots are shaped to allow at least some of said tabs to slide laterally along corresponding ones of said slots until vertical movement of said tab with respect to the disposable portion is reduced when said sensor is applied to said patient.

6. The noninvasive optical oximetry sensor of claim 1, wherein said slots comprises a rigid material.

7. A method of assembling a noninvasive optical oximetry sensor, the method comprising:
   providing a disposable element of a sensor including an attachment mechanism configured to removably attach to a patient at a measurement site and a plurality of slots;
   providing a reusable element of said sensor, the reusable element including a flex circuit, a light source, one or more detectors configured to detect light from said light source after attenuation by said tissue and output said signals responsive to said detected light, a plurality of conductors proximate said flex circuit, some of said conductors communicating with said light source and others of said conductors communicating with said one or more detectors, a protective coating encasing at least said light source, said one or more detectors and at least some of said conductors and some of said flex circuit, and tabs proximate at least said light source and said one or more detectors, said tabs configured to mate with said slots of said disposable element where at least some of said tabs can move within corresponding mated slots to self-adjust the disposable element and the reusable element with respect to one another when the disposable element is applied to said patient after sensor assembly; and
   positioning the tabs within the slots.

8. The method of claim 7, wherein said providing said reusable element including said protective coating comprises providing said reusable element including a flexible protective coating.

9. The method of claim 8, wherein said providing said reusable element including said flexible protective coating comprises providing said reusable element including a flexible protective coating comprising rubber.

10. The method of claim 8, wherein said providing said reusable element including said flexible protective coating comprises providing said reusable element including a flexible protective coating comprising plastic.

11. The method of claim 7, wherein said providing said reusable element, including said protective coating comprises providing said reusable element including said protective coating having apertures providing a light path from said light source or said detector to said measurement site.

12. The method of claim 7, wherein said providing said disposable element comprises providing said disposable element including at least some of said slots sized to allow said tabs to slide laterally within corresponding said slots until vertical movement of said tab with respect to the disposable portion is reduced when said sensor is applied to said patient.

* * * * *